US005405966A

United States Patent [19]

Theodore et al.

[11] Patent Number: 5,405,966

[45] Date of Patent: Apr. 11, 1995

[54] TRICHOTHECENE CONJUGATES

[76] Inventors: Louis J. Theodore, 622 152nd Pl., SW., Lynnwood, Wash. 98037; John M. Reno, 2452 Elm Dr., Brier, Wash. 98036; Sudhakar Kasina, 13710 115th Ave. NE., Kirkland, Wash. 98034; James A. Sanderson, 1539 NE. 103rd Ave., Seattle, Wash. 98125; Paul G. Abrams, 2125 First Ave., #1602, Seattle, Wash. 98121

[21] Appl. No.: 73,118

[22] Filed: Jun. 7, 1993

Related U.S. Application Data

[63] Continuation-in-part of Ser. No. 943,184, Sep. 10, 1992, abandoned, which is a continuation of Ser. No. 194,642, May 16, 1988, Pat. No. 5,157,104, which is a continuation-in-part of Ser. No. 788,325, Oct. 17, 1985, Pat. No. 4,744,981.

[51] Int. Cl.[6] .................... C07D 209/76

[52] U.S. Cl. .................... 548/526; 548/520; 546/270; 546/256

[58] Field of Search .................... 548/526, 520

[56] References Cited

U.S. PATENT DOCUMENTS

| | | | |
|---|---|---|---|
| 4,507,234 | 3/1985 | Kato et al. | 514/2 |
| 4,618,585 | 10/1986 | Chan | 435/172.2 |
| 4,624,846 | 11/1986 | Goldenberg | 424/1.1 |

FOREIGN PATENT DOCUMENTS

| | | |
|---|---|---|
| 074279 | 3/1983 | European Pat. Off. . |
| 088695 | 9/1983 | European Pat. Off. . |
| 220065 | 4/1987 | European Pat. Off. . |

OTHER PUBLICATIONS

F. S. Chu et al., *Appl. Environ. Microbiol.*, 1984, 48 (4), pp. 781–784 "Production and Characterization of Antibody Against Deoxyverrucarol".

K. W. Hunter, Jr. et al., *Chem. Abstr.* 102:76957n (1985), "Preparation and characterization of monoclonal antibodies to the trichothecene mycotoxin T-2".

J. R. Bamburg, Prog. Molec. Subcell. Biol. 8:41–110 (1983), "Biological and Biochemical Actions of Trichothecene Mycotoxins".

J. W. Uhr, *J. Immunol.* 133:i–x (1984), "Immunotoxins: Harnessing Nature's Poisons".

B. M. J. Foxwell, Immunotoxicology, Academic Press, London, (1983) pp. 359–368 "Monoclonal antibody-toxin conjugates as selective cytotoxic agents".

*Protection Against Trichothecene Mycotoxins*, National Academy Press, Washington, D.C., (1983), pp. 17–20; 129–136, "The Trichothecene Mycotoxins: Their Structure, Natural Production, and Levels of Occurrence".

Murphy et al., *Cancer Treatment Rep.*, 62, (1978), pp. 1497–1502, "Phase I Clinical Evaluation of Anguidine".

Adler et al., *Cancer Treatment Rep.*, 68 (1984), pp. 423–425, "Anguidine: A Broad Phase II Study of the Southeastern Cancer Study Group".

Heikkila et al., *J. Biol. Chem.*, vol. 262, 34, Dec. 5, 1987, pp. 16456–16460, "Bomesin-related peptides induce calcium mobilization in a subset of human small cell lung cancer cell lines".

Kris et al., *J. Biol. Chem.*, vol. 262, 23, Aug. 15, 1987, pp. 11215–11220, "Identification of the bombesin receptor on murine and human cells by cross-linking experiments".

(List continued on next page.)

*Primary Examiner*—Jane T. Fan

[57] ABSTRACT

Conjugates of trichothecenes and agents that bind to a defined population of cells are disclosed. Preferred are conjugates of trichothecene molecules with polyclonal or monoclonal antibodies or fragments thereof that recognize antigens that are present only on tumor cells or are augmented in their expression on tumor cells as compared to normal tissues. Trichothecene molecules are coupled to the agent through non-covalent and covalent linkages, such as peptide bonds, disulfide bonds, thioester bonds, or thioether bonds. A method for inhibiting the growth and metabolism of antigen-positive cells is also disclosed. Derivatized trichothecene compounds prepared for conjugation to targeting agents are also disclosed.

7 Claims, No Drawings

OTHER PUBLICATIONS

Carney et al., *Cancer Research*, 47, Feb. 1, 1987, pp. 821–825, "Selective stimulation of small cell lung cancer clonal growth by bombesin and gastrin-releasing peptide".

Sausville et al., *J. Biol. Chem.*, vol. 261, 5, Feb. 15, 1986, pp. 2451–2457, "Expression of the gastrin-releasing peptide gene in human small cell lung cancer".

Gargosky et al., *Biochem J.* (1987) vol. 247, pp. 427–432 (printed in Great Britain), "C-Terminal bombesin sequence requirements for binding and effects on protein synthesis in Swiss 3T3 cells".

A. Huntley Blair and Tarun I. Ghose, *J. Immunol. Meth.* (1983) vol. 59, pp. 129–143, "Linkage of cytotoxic agents to immunoglobulins".

Carlsson, J. et al., "Protein Thiolation and Reversible Protein-Protein Conjugation, N-Succinimidyl 3-(2-Pyridyldithio)Propionate, A New Heterobifunctional Reagent", *Biochem J.*, vol. 173, pp. 723–737, 1978.

Anderson, D. W. et al., "Structure-Activity Studies of Trichothecenes: Cytotoxicity of Analogues and Reaction Products Derived from T-2 Toxin and Neosolaniol", *J. Med. Chem.*, vol. 32, pp. 555–562, 1989.

Kaneko, T. et al., "Structural Modifications of Anguidin and Antitumor Activities of its Analogues", *J. Med. Chem.*, vol. 25, pp. 579–589, 1982.

Geoghegan, K. F. et al., "Site-Directed Conjugation of Nonpeptide Groups to Peptides and Proteins via Periodate Oxidation of 2-Amino Alcohol. Application to Modification at N-Terminal Serine", *Bioconjugate Chem.*, vol. 3, pp. 138–146, 1992.

Braslawsky, G. R. et al., "Antitumor Activity of Adriamycin (Hydrozone-linked) Immunoconjugates compared with Free Adriamycin and Specificity of Tumor Cell Killing", *Cancer Research*, vol. 50, pp. 6608–6614, 1990.

Jarvis, B. B. et al., "Antileukemic Compounds Derived by Chemical Modification of Macrocyclic Trichothecenes. 2. Derivatives of Roridins A and H and Verrucarins A and J", *J. Med. Chem.*, vol. 27, pp. 239–244, 1984.

Jarvis, B. B. and Mazzola, E. P., "Macrocyclic and Other Novel Trichothecenes: Their Structure, Synthesis, and Biological Significance", *Acc. Chem. Res.*, vol. 15, pp. 388–395, 1982.

*Tricothecene Mycotoxicosis: Pathophysiologic Effects*, vol. I, V. R. Beasley (ed.), CRC Press, Boca Raton, Fla., 1989, Chapter 5, pp. 73–105, Jarvis, B. B. and Acierio, A. M., "Anticancer Properties of Trichothecens".

*Medicinal Chemistry*, Cassidy, J. M. and Douros, J., vol. 16, Chapter 2, pp. 43–72, New York, Academic Press, 1980, Doyle, T. W. and Bradner, W. T., "Trichothecanes".

TRICHOTHECENE CONJUGATES

CROSS REFERENCE TO RELATED APPLICATIONS

This application is a continuation-in-part of application Ser. No. 07/943,184 filed Sep. 10, 1992, now abandoned which in turn is a continuation of application Ser. No. 07/194,642, filed May 16, 1988, which issued Oct. 20, 1992, as U.S. Pat. No. 5,157,104, which in turn is a continuation-in-part of application Ser. No. 788,325, filed Oct. 17, 1985, which issued May 17, 1988 as U.S. Pat. No. 4,744,981.

TECHNICAL FIELD

The present invention relates generally to the conjugation of molecules to agents that bind to a defined population of cells and more specifically, to conjugates of agents such as antibodies with trichothecenes and to methods for using these conjugates.

BACKGROUND ART

The use of antibodies as carriers for toxic agents to kill tumor cells selectively has depended upon the coordination of research in three distinct areas: (a) the development of polyclonal or monoclonal antibodies (and their fragments) with specificity for a defined population of cells, such as tumor cells; (b) the elucidation of the chemistry of toxic molecules and the conditions appropriate for their linkage to antibodies; and (c) the production and isolation of naturally occurring toxic molecules. Conjugates of monoclonal antibodies with drugs, plant toxins, and ribosomal inactivating proteins have been summarized by Morgan and Foon, (Monoclonal Antibody Therapy of Cancer: Preclinical Models and Investigations; *Basic and Clinical Tumor Immunology*, Vol. 2, Kluwer Academic Publishers, Hingham, Mass.) and Uhr (*Journal of Immunology* 133:i-vii, 1984). Interest in the potent higher plant toxin molecules peaked with the *Immunology* 133:i-vii, 1984). Interest in the potent higher plant toxin molecules peaked with the development of monoclonal antibodies because it appeared that the latter could be used as highly specific targeting agents for these toxins.

In general, the higher molecular weight toxins have characteristic A and B chains, with the B chain responsible for binding (usually via lectins to oligosaccharides) and A chains that act catalytically to irreversibly inhibit elongation factor 2 (EF2), therefore preventing protein synthesis. The vision was that the specificity of the antibody could substitute for the non-specific binding of B chain and deliver A chain selectively to tumor cells. More recently, a class of compounds called "ribosomal inactivating proteins" (RIPs) have been discovered that represent the equivalent of A chains without any associated B chain.

A number of obstacles emerged, however, that compromised the realization of this simple vision. First, it was apparent that it was critical to develop systems to remove B chain from A chain beyond purity achieved with simple affinity chromatography. The RIPs and cloned toxins represent one practical solution to this problem. Second, the reticulo-endothelial system removes macromolecules from the circulation, especially those that have been altered, such as an antibody that has been bound to toxin. Third, it became apparent that there were receptors for the carbohydrates that exist naturally on the protein plant toxins. These also contributed to non-specific uptake and, therefore, toxicity. Finally, it became clear that B chain was critical for more than just binding to the cell, and seemed to facilitate the translocation of the A chain into the cell and eventually into the cytoplasm, where it effected it cytotoxicity.

Due to these obstacles, there is a need in the art for a class of conjugates that overcome the problems noted above, while concurrently possessing the capability of killing defined populations of cells, such as tumor cells, on a selective basis. The present invention fulfills this need and further provides other related advantages.

DISCLOSURE OF THE INVENTION

Briefly stated, the present invention discloses conjugates of trichothecenes and agents that bind to a defined population of cells. Preferred are conjugates of trichothecene molecules with polyclonal or monoclonal antibodies or fragments thereof that recognize antigens that are present only on tumor cells or are augmented in their expression on tumor cells as compared to normal tissues.

In accordance with the present invention, "trichothecenes" are defined to include molecules derived from *fungi imperfecti, baccharus megapotamica* or prepared synthetically or synthesized from fungal products that have as their common characteristic a sesquiterpenoid central ring structure and its simple and macrocyclic derivatives.

The trichothecene molecules are coupled to the agent through non-covalent and covalent linkages, preferably a covalent linkage, such as a peptide bond, a disulfide bond, an ester bond, a thioester bond, or a thioether bond. This covalent linkage may be formed between: (a) a trichothecene hemisuccinate carboxylic acid; (b) a trichothecene hemisuccinate N-hydroxysuccinimidate ester; (c) trichothecene dithio N-hydroxysuccinimidate ester; (d) trichothecene thio N-hydroxysuccinimidate ester; (e) trichothecene oxime N-hyroxysuccinimidate ester; or (f) trichothecene hydrazone M-hyroxysuccinimidate ester, or any polymeric carrier, and one or more sulfhydryl groups of the agent; (g) trichothecene pyridinyldithio propanoic acid hydrazones; (h) trichothecene pyridinyldithio propanoic acid oxime; (i) trichothecene/poly-L-lysine complexes, or any polymeric carrier, and one or more amino groups of the agent.

A related aspect of the present invention is directed toward a method for inhibiting the growth and metabolism of antigen positive cells, comprising exposing the antigen positive cells to a conjugate of a trichothecene and an agent that binds to the antigen positive cells.

Other aspects of the invention will become evident upon reference to the following detailed description.

BEST MODE FOR CARRYING OUT THE INVENTION

"Trichothecenes" are a species of mycotoxins produced by soil fungi of the class *fungi imperfecti* or isolated from *baccharus megapotamica* (Bamburg, J. R., *Proc. Molec. Subcell. Bio.* 8:41-110, 1983; Jarvis & Mazzola, *Acc. Chem. Res.* 15:338-395, 1982). They appear to be the most toxic molecules that contain only carbon, hydrogen and oxygen (Tamm, C., *Fortschr. Chem. Org. Naturst.* 31:61-117, 1974). They all act at the level of the ribosome as inhibitors of protein synthesis, either at the initiation, elongation or termination phases. As small molecules (ca. 4–600 MW), they have potential advantages:

1) improved delivery due to only minor changes in the molecular weight of antibody;
2) lack of receptor mediated, non-specific uptake, e.g., via carbohydrate receptors, a drawback of higher molecular weight (ca. 30,000 MW) plant toxins, like ricin A chain, or ribosomal inactivating proteins, such as gelonin.

Similar to toxins, however, mycotoxins can be extremely potent. They are the most potent small molecule inhibitors of protein synthesis in eucaryotic cells. Unconjugated to antibody, verrucarin A (Table 4) is 10-fold or greater more potent than actinomycin D, the most potent per weight of the chemotherapeutic drugs currently approved for clinical use. Since most currently used drugs act at the level of DNA, these ribosomal inactivating drugs, like toxins, should not be adversely affected by resistance to "standard" drugs, and should produce additive cytotoxicity to existing therapies.

There are two broad classes of trichothecenes: those that have only a central sesquiterpenoid structure and those that have an additional macrocyclic ring (simple and macrocyclic trichothecenes, respectively). The simple trichothecenes may be subdivided into three groups. Group A simple trichothecenes may be characterized by the formula:

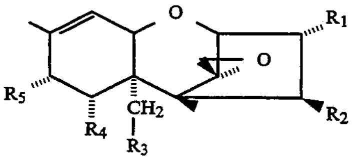

wherein $R_1$ is H, OH, or $$O-\overset{\overset{O}{\|}}{C}-CH_3;$$

$R_2$ is H, OH, or $$O-\overset{\overset{O}{\|}}{C}-CH_3;$$

$R_3$ is H, OH, or $$O-\overset{\overset{O}{\|}}{C}-CH_3;$$

$R_4$ is H or OH; and
$R_5$ is H, OH, $$O-\overset{\overset{O}{\|}}{C}-CH_3,\ \text{or}\ \overset{\overset{O}{\|}}{C}-O-CH_2CH(CH_3)_2.$$

Representative Group A simple trichothecenes and corresponding functional groups are listed in Table 1.

TABLE 1

| | Group A Simple Trichothecenes | | | | |
|---|---|---|---|---|---|
| Trichothecenes | $R_1$ | $R_2$ | $R_3$ | $R_4$ | $R_5$ |
| Trichothecene (scirpene) | H | H | H | H | H |
| Trichodermol (roridin C) | H | OH | H | H | H |
| Dihydrotrichothecene | H | H | OH | H | OH |
| Scirpen-4,8-diol | H | OH | H | H | OH |
| Verrucarol | H | OH | OH | H | H |
| Scirpentriol | OH | OH | OH | H | H |
| T-2 tetraol | OH | OH | OH | H | OH |
| Pentahydroxyscirpene | OH | OH | OH | OH | OH |
| 4-Deacetylneosolaniol | OH | OH | OH | H | OH |
| Trichodermin | H | OAc | H | H | H |
| Deacetylcalonectrin | OAc | H | OH | H | H |
| Calonectrin | OAc | H | OAc | H | H |
| Diacetylverrucarol | H | OAc | OAc | H | H |
| 4-Monoacetoxy-scirpenol | OH | OAc | OH | H | H |
| 4,15-Diacetoxy-scirpenol (DAS) | OH | OAc | OAc | H | H |
| 7-Hydroxydiacetoxy-scirpenol | OH | OAc | OAc | OH | H |
| 8-Hydroxydiacetoxy-scirpenol (neosolaniol) | OH | OAc | OAc | H | OH |
| 7,8-Dihydroxy-diacetoxy-scirpenol | OH | OAc | OAc | OH | OH |
| 7-Hydroxy-8-acetyl-diacetoxy-scirpenol | OH | OAc | OAc | OH | OAc |
| 8-Acetylneosolaniol (8-Acetyl-DAS) | OH | OAc | OAc | H | OAc |
| NT-1 | OH | OAc | OH | H | OAc |
| NT-2 | OH | OAc | OH | H | OH |
| HT-2 toxin | OH | OH | OAc | H | OCO—$CH_2CH(CH_3)_2$ |
| T-2 toxin | OH | OAc | OAc | H | OCO—$CH_2CH(CH_3)_2$ |
| Acetyl T-2 toxin | OH | OAc | OAc | H | OCO—$CH_2CH(CH_3)_2$ |

Group B simple trichothecenes may be characterized by the formula:

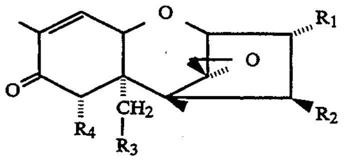

wherein $R_1$ is H, OH, $$O-\overset{\overset{O}{\|}}{C}-CH_3;$$

or $R_2$ is H, OH, $$O-\overset{\overset{O}{\|}}{C}-CH_3,\ \text{or}\ O-\overset{\overset{O}{\|}}{C}-CH=CH-CH_3;$$

$R_3$ is H, OH, or $$O-\overset{\overset{O}{\|}}{C}-CH_3;$$

and $R_4$ is H, OH, or

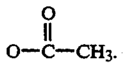

Representative Group B simple trichothecenes and corresponding functional groups are listed in Table 2.

TABLE 2

| Group B Simple Trichothecenes | | | | |
|---|---|---|---|---|
| Trichothecenes | $R_1$ | $R_2$ | $R_3$ | $R_4$ |
| Trichothecolone | H | OH | H | H |
| Trichothecin | H | OCOCH=CHCH3 | H | H |
| Deoxynivalenol (DON) | OH | H | OH | OH |
| 3-Acetyldeoxynivalenol | OAc | H | OH | OH |
| 5-Acetyldeoxynivalenol | OH | H | OH | OAc |
| 3,15-Diacetyldeoxynivalenol | OAc | H | OAc | OH |
| Nivalenol | OH | OH | OH | OH |
| 4-Acetylnivalenol (fusarenon-X) | OH | OAc | OH | OH |
| 4,15-Deacetylnivalenol | OH | OAc | OAc | OH |
| 4,7,15-Triacetylnivalenol | OH | OAc | OAc | OAc |
| Tetracetylnivalenol | OAc | OAc | OAc | OAc |

Group C simple trichothecenes may be characterized by the formula:

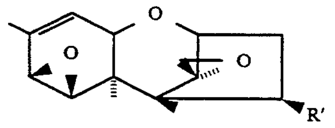

wherein R' is OH or

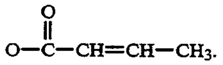

Representative Group C simple trichothecenes and corresponding R' functional groups are listed in Table 3.

TABLE 3

| Group C Simple Trichothecenes | |
|---|---|
| Trichothecenes | R' |
| Crotocol | OH |
| Crotocin | OCOCH=CHCH3 |

The macrocyclic trichothecenes may be characterized by the formula:

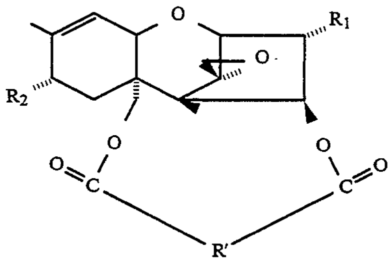

wherein $R_1$ is OH or

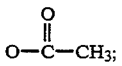

R2 is H, OH,

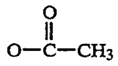

or $OCOCH_2CH(CH_3)_2$; and R' is:

TABLE 4

| R' | Representative Macrocyclic Trichothecenes |
|---|---|
| 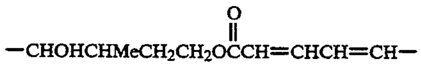 | Verrucarin A |
| 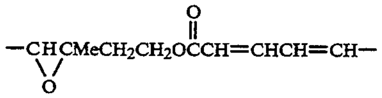 | Verrucarin B |
| 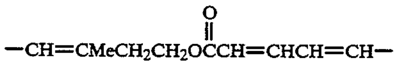 | Verrucarin J (Satratoxin C) |
| 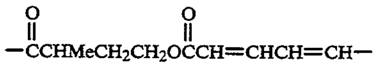 | 2-Dehydro-verrucarin A |
| 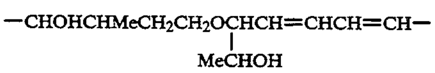 | Roridin A |
| 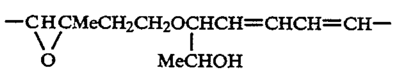 | Roridin D |

TABLE 4-continued

| R′ | Representative Macrocyclic Trichothecenes |
|---|---|
| 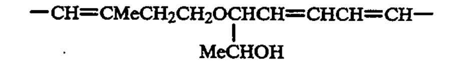 | Roridin E (Satratoxin D) |
| 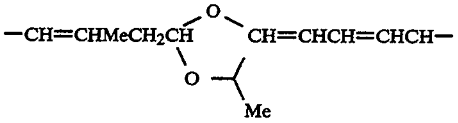 | Roridin H |
| 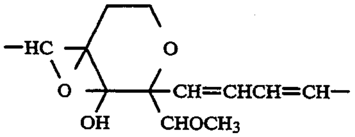 | Satratoxin F |
| 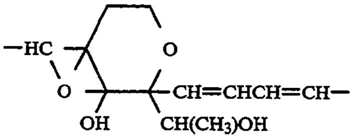 | Satratoxin G |
| 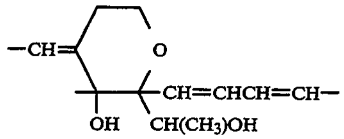 | Satratoxin H |
| 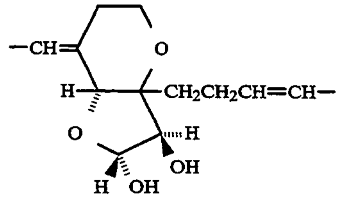 | Vertisporin |

The sesquiterpenoid ring functions in a manner similar to the A chains of plant toxins, in binding to ribosomes and inhibiting protein synthesis. The macrocyclic ring enhances cell binding and internalization in an unknown manner. There are molecules in each class that, while potent inhibitors of translation in cell-free systems, are only minimally cytotoxic ($ID_{50}=10$ μg/ml) to eucaryotic cells.

Variations in ribosome binding ability are not well correlated with cytotoxicity, strongly suggesting that differential delivery to ribosomes in the cell or intracellular deactivation may play an important role in the activities of these drugs against eucaryotic cells (Bamburg, J. R., Biological and Biochemical actions of Trichothecene Mycotoxins, *Prog. Mol. Subcell. Biol.* 8:41-110, 1983; McLaughlin, C. S., Vaughan, M. H., Cambell, I. M., Wei, C. M., Stafford, M. E., and Hansen, B. S., Inhibition of Protein Synthesis by Trichothecenes, In: *Mycotoxins in Human and Animal Health,* Pathotox Publishers, Park Forest South, Ill., pp. 263-273, 1977; and Doyle, T. W., and Bradner, W. T., Trichothecenes, In: *Anticancer Agents Based on Natural Product Models* [Cassidy and Bouros, Eds.], Academic Press, Inc., New York, N.Y., pp. 43-72, 1980). It is possible, for example, that verrucarol binds poorly to cell membranes, or may be deactivated intracellularly, deficiencies that may be overcome by conjugation to monoclonal antibodies. There have been some studies of the rates at which certain of the trichothecenes are converted into biologically inactive molecules (apotrichothecenes) by intracellular acid catalysis as might occur in lysosomes. The macrocyclic trichothecenes and some simple trichothecenes, such as anguidine and T-2 toxin, are inactivated quite slowly, whereas less cytotoxic molecules, such as verrucarol, are inactivated more quickly. There is an inverse linear correlation between cytotoxicity and the rate of this rearrangement into apotrichothecenes.

Anguidine, a simple trichothecene, has been tested in Phase I (Murphy, W. K., Burgess, M. A., Valdivieso, M., Livingston, R. B., Bodey, G. P., and Freireich, E. J., Phase I Evaluation of Anguidine, *Cancer Treat. Repts.* 62:1497, 1978) and Phase II (Adler, S. S., Lowenbraun, S., Birch, B., Jarrell, R., and Garrerd, J., Anguidine: A Broad Phase II Study of the Southeastern Cancer Study Group, *Cancer Treat. Repts.* 68:423, 1984) clinical trials in patients. The overall tumor response rate was low and there was considerable hematologic toxicity in the Phase II trial. In the Phase I trial, toxicity included nausea, vomiting, hypotension,.central nervous system symptoms, diarrhea, chills and fever, generalized burning erythema, stomatitis, shortness of breath, moderate myelosuppression with an association between life threatening toxicity and the presence of liver metastases or impairment of liver function recognized at higher doses.

The trichothecenes of the present invention may be conjugated to a targeting agent. A targeting agent has the capacity to bind to a defined population of cells. The targeting agent may bind through a receptor, substrate, antigenic determinant, or other binding site on the target cell population.

Preferred targeting agents useful within the present invention include antibody and antibody fragments, such as internalizing antibody; peptides, such as bombesin, gastrin-releasing peptide, RGD peptide, substance P, neuromedin-B, neuromedin-C, and metenkephalin; and hormones, such as estradiol, neurotensin, melanocyte stimulating hormone, follicle stimulating hormone, leutenizing hormone, and human growth hormone. Other suitable targeting agents include serum proteins, fibrinolytic enzymes, and biological response modifiers, such as interleukin, interferon, erythropoietin and colony-stimulating factor. Analogs of the above-listed targeting agents that retain the ability to bind to the defined target cell population may also be used within the claimed invention. In addition, synthetic targeting proteins and peptides may be designed and made to "fit" a particular, characterized epitope (binding site). That is, a synthetic targeting protein/peptide would be designed to bind a specific epitope in a "lock and key" fashion. Within the present invention, antibody and antibody fragments (including surface antigen bound antibody and internalizing antibody), bombesin and gastrin-releasing peptide and their analogs are particularly preferred targeting agents. Exemplary internalizing antibodies include humanized α-TAC, murine and humanized anti-CD33, anti-PEM (for breast and ovarian), anti-colon, or any other like antibodies.

The linkage of trichothecene molecules to polyclonal and monoclonal antibodies or fragments thereof that recognize antigens that are augmented in their expression on tumor cells as compared to normal tissues may be divided into two distinct strategies: (1) linking poorly-cytotoxic trichothecenes to antibodies or fragments thereof in order to render them cytotoxic; and (2) conjugating cytotoxic trichothecenes to antibodies or fragments thereof to deliver them selectively to tumor cells, sparing normal tissues most of their toxicity.

Within the present invention, monoclonal antibodies were prepared by immunizing rodents or other animals and/or are developed by harvesting human lymphocytes from patients bearing malignancies and immortalizing the antibody secretion of the cells by standard hybridoma technology (Geffer et al., *Somatic Cell Genet.* 3:231, 1977). Alternatively, polyclonal antiserum is prepared by harvesting serum from animals following immunization with tumor cells or other defined tumor-associated antigens or harvesting from humans who have or have had exposure to tumors or tumor-associated antigens, and subjecting the serum to standard purification techniques. Antibodies were screened for specificity using standard radioimmunoassay or enzyme-linked immunosorbent assay (ELISA) against the appropriate targets. Screening was performed with normal human tissues to select antibody with appropriate tumor specificity.

After purification of the desired antibody species, the antibodies were conjugated to the trichothecene molecules. The carboxylic acid of the trichothecene hemisuccinate was linked to the amino groups of the antibody using a carbodiimide. Alternatively, N-hydroxy succimidate ester of the trichothecene hemisuccinate is prepared and used to link to the amino groups of the antibody. Both of these methods result in an amide bond between the trichothecene and the antibody. Thioether can also be used as a stable bond between the antibody and the trichothecene. In addition, the trichothecene molecules are linked to poly-L-lysine (MW 300 to 150,000). The poly-L-lysine/trichothecene complex is then linked to the antibody via an amide bond. Also, when a more labile bond seems desirable, the trichothecene is linked by a disulfide or a thioester bond to the monoclonal antibody (MA).

The immunoconjugates were easily separated from the unreacted trichothecene by FPLC gel filtration using a TSK 3000 column. Alternatively, the unreacted trichothecene is removed by dialysis and/or by PD-10 (gel filtration, Sephadex® G-25 [Pharmacia, Piscataway, N.J.]) column.

The molecular weight of the conjugate will not be significantly greater than that of the free antibody. Therefore, separation of the immunoconjugate from free antibody requires use of hydroxyapatite, hydrophobic column chromatography or ion exchange chromatography.

Conjugates were analyzed by isoelectric focusing (IEF) and SDS-PAGE. IEF is a measure of the degree of substitution and resulting charge of the antibody. SDS-PAGE separates proteins on the basis of molecular weight and is used to assess the covalent aggregates formed during the conjugation process. The conjugate is compared to the unconjugated antibody for immune reactivity that is quantified by flow cytometry. The immunoconjugates are incubated with antigen positive cells, washed, and then the cells are incubated with fluorescein isothiocyanate-linked goat anti-mouse antibody. Cell bound fluorescence is read on a flow cytometer and mean fluorescence index is calculated. Competition is performed using a standard unconjugated antibody preparation in comparison for inhibition with the conjugate. Similar analyses, employing antigen negative cells, were used to demonstrate the retention of specificity of the conjugate for antigen positive cells.

Cytotoxicity of the immunoconjugates was assessed with two methods. A colorimetric assay employs 3-(4,5-dimethylthiazol-2-yl)-2,5-diphenyl tetrazolium bromide as the substrate. This substance is cleaved by living cells to yield a dark blue formazan product. This process requires active mitochondria. The substrate (MTT) was solubilized and read on an ELISA reader. This assay has an excellent correlation with the standard $^{3}$H-thymidine incorporation assay and avoids the use of radioactivity. $^{3}$H-thymidine was reserved for confirmation of major results.

Potency and selectivity assays were performed by incubating conjugates with antigen positive and antigen negative cell lines. Conjugates were added to the cells at varying concentrations and cell survival assessed after continuous and short exposure times. The conjugates were incubated with the cells for three days for continuous exposure and for two hours for the short exposure. At the end of three days, cell survival was assessed.

The conjugates were also tested for their ability to inhibit peptidyl transferase. The assay is based upon competition with radiolabeled trichodermin for the binding site on the 60S ribosome. Conjugates were also tested for their ability to inhibit protein synthesis using natural mRNA to determine their overall effect on protein synthesis and a poly U to measure the effect on elongation.

The present invention further provides derivatized trichothecene compounds for conjugation to targeting agents. Conjugation of these derivatized trichothecenes may be conducted through either of two exemplary schemes: (1) reaction of the amino groups of a targeting moiety with N-hydroxysuccinimidate-derivatized trichothecenes or (2) the reaction of reduced disulfides or free sulfhydryls of a targeting moiety with 2-pyridinyl-dithio-derivatized trichothecenes.

Exemplary simple trichothecenes useful in the practice of this and other aspects of the present invention are as follows:

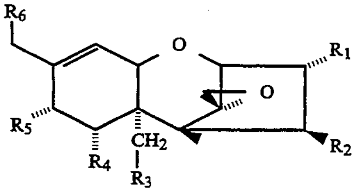

wherein:

$R_1$ is H, OH,

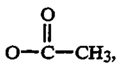

SH or $L_1$, $L_2$, $L_3$, or $L_4$;

$R_2$ is H, OH, or

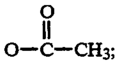

$R_3$ is H, OH, or

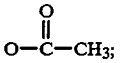

$R_4$ is H, or forms an epoxide group with $R_5$;

$R_5$ is H, OH,

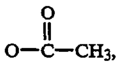 , 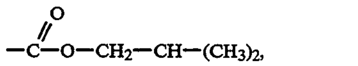

SH, $OCH_3$, $SCH_3$, $NH_2$, $NHCH_3$, $N(CH_3)_2$, $L_3$, $L_4$, or forms an epoxide group with $R_4$; and $R_6$ is H, OH, SH, $OCH_3$, $SCH_3$, $NH_2$, $NHCH_3$, $N(CH_3)_2$, $L_3$, or $L_4$ provided that at least one of $R_1$, $R_5$ and $R_6$ is $L_1$, $L_2$, $L_3$, or $L_4$ and further provided that $R_5$ and $R_6$ are not $L_1$ or $L_2$ and wherein $L_1$ is 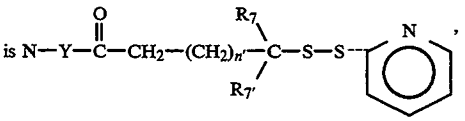 , -continued $L_2$ is 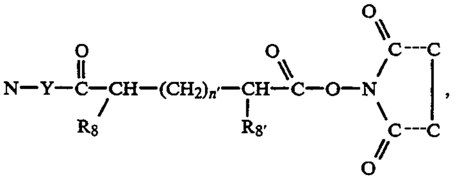 , $L_3$ is 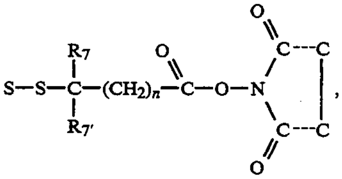 , or $L_4$ is 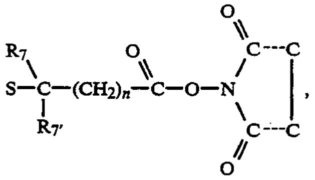 , and wherein Y is O or NH, $R_7$ or $R_{7'}$ is H or $CH_3$, $R_8$ or $R_{8'}$ is H or OH, n is one to ten; and n' is zero to ten.

Preferred simple trichothecenes are compounds where $R_2$ and $R_3$ are both

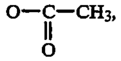

and $R_4$ and $R_5$ are both H. More preferred trichotthecenes are characterized as follows:

(1) $R_1$ is $L_1$ or $L_2$ and Y is NH, $R_7$ and $R_{7'}$ are independently either H or $CH_3$, $R_8$ and $R_{8'}$ are independently either H or OH, and n' is zero to ten; further provided that $R_2$ and $R_3$ are both

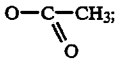

$R_4$ is H; and $R_5$ and $R_6$ are selected from the group consisting of H, OH, SH, $OCH_3$, $SCH_3$, $NH_2$, $NHCH_3$, $N(CH_3)_2$;

(2) $R_1$ is H, OH or SH; and $R_5$ and $R_6$ are selected from the group consisting of H, OH, SH, $OCH_3$, $SCH_3$, $NH_2$, $NHCH_3$, $N(CH_3)_2$, and $L_3$, wherein $R_7$ and $R_{7'}$ are independently either H or $CH_3$ and n is one to ten;

(3) $R_1$ is H, OH or SH; and $R_5$ or $R_6$ is selected from the group consisting of H, OH, SH, $OCH_3$, $SCH_3$, $NH_2$, $NHCH_3$, $N(CH_3)_2$, and $L_4$, wherein n is one to ten, and $R_7$ and $R_{7'}$ are independently either H or $CH_3$;

(4) $R_1$ is $L_3$ or $L_4$ wherein $R_7$ and $R_{7'}$ and independently either H or $CH_3$ and n is one to ten; and $R_5$ and $R_6$ are selected from the group consisting of H, OH, SH, $OCH_3$, $SCH_3$, $NH_2$, $NHCH_3$, $N(CH_3)_2$.

A prototypical simple trichothecene is anguidine or the 3-keto derivative thereof. Within the context of the above presented structures a prototypical simple trichothecene is characterized as follows: $R_1$ is $L_1$ and Y is NH, $R_7$ and RT, are both H, and n' is zero; $R_4$, $R_5$, $R_6$ are H; and $R_2$ and $R_3$ are both

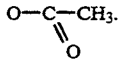

Exemplary macrocyclic trichothecenes useful in the practice of this and other aspects of the present invention are as follows:

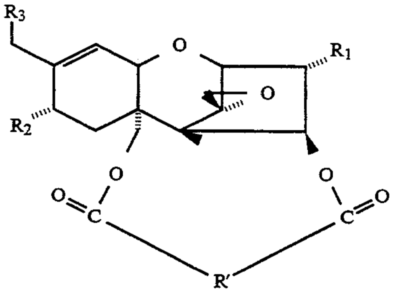

wherein R' is selected from the group consisting of

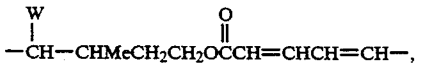

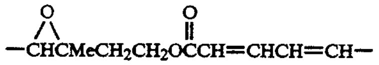

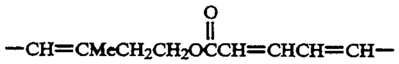

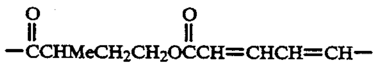

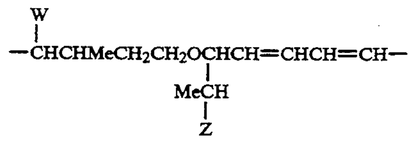

provided at least one of $R_1$, W and Z is $L_1$, $L_2$, $L_3$, or $L_4$, and further provided W and Z are not both $L_1$, $L_2$, $L_3$, or $L_4$ wherein $L_1$ is

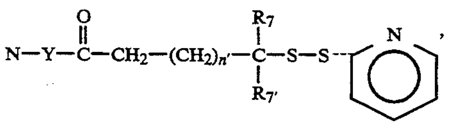

$L_2$ is

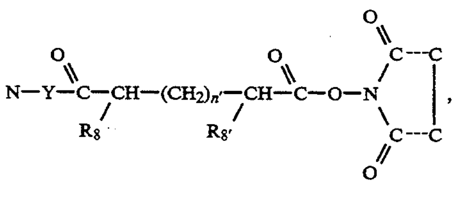

$L_3$ is

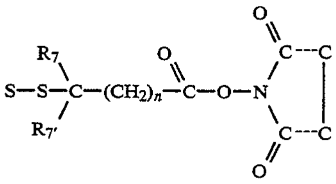

, or $L_4$ is

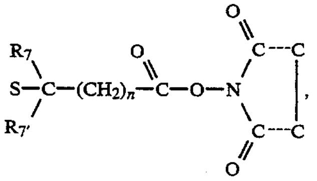

and wherein

Y is O or NH, $R_7$ or $R_{7'}$ is H or $CH_3$, $R_8$ or $R_{8'}$ is H or OH, n is one to ten; and N' is zero to ten;

and further provided that W can be an epoxide group between 2' and 3' and still further provided that W and Z can be independently either H, OH, or SH when W and Z are not $L_1$, $L_2$, $L_3$, or $L_4$; $R_1$ is H, OH, or SH when $R_1$ is not $L_1$, $L_2$, $L_3$, or $L_4$; and $R_2$ and $R_3$ are selected from the group consisting of H, OH, SH, $OCH_3$, $SCH_3$, $NH_2$, $NHCH_3$, $N(CH_3)_2$, $L_3$ and $L_4$.

Preferred macrocyclic trichothecenes are compounds wherein R' is

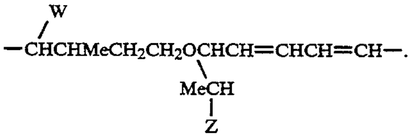

Such preferred compounds are derivatives of Roridin A. More preferred macrocyclic trichothecenes of this type are characterized as follows:

(1) $R_1$ is $L_1$, $L_2$, $L_3$, or $L_4$ wherein

Y is O or NH, $R_7$ and $R_{7'}$ are independently either H or $CH_3$, $R_8$ and $R_{8'}$ are independently either H or OH, n is one to ten, n' is zero to ten;

when $R_2$ and $R_3$ are selected from the group consisting of H, OH, SH, $OCH_3$, $SCH_3$, $NH_2$, $NHCH_3$, $N(CH_3)_2$; and W and Z are independently either H, OH, or SH;

(2) $R_1$ and W are independently either H, OH, or SH; $R_2$ and $R_3$ are selected from the group consisting of H, OH, SH, $OCH_3$, $SCH_3$, $NH_2$, $NHCH_3$, $N(CH_3)_2$; and Z is $L_1$, $L_2$, $L_3$, or $L_4$ and wherein Y is O or NH, $R_7$ or $R_{7'}$ is H or $CH_3$, $R_8$ or $R_{8'}$ is H or OH, n is one to ten; and n' is zero to ten;

(3) $R_1$ and Z are H, SH, or OH; $R_2$ and $R_3$ are selected from the group consisting of H, OH, SH, $OCH_3$, $SCH_3$, $NH_3$, $NHCH_3$, $N(CH_3)_2$; and W is either $L_1$, $L_2$, $L_3$, or $L_4$ and wherein Y is O or NH,
$R_7$ or $R_{7'}$ is H or $CH_3$,
$R_8$ or $R_{8'}$ is H or OH,
n is one to ten, and
n' is zero to ten; and (4) $R_1$, W and Z are independently either SH or OH; $R_2$ and $R_3$ are selected from the group consisting of H, OH, SH, $OCH_3$, $SCH_3$, $NH_2$, $NHCH_3$, $N(CH_3)_2$, $L_3$, and $L_4$ wherein
$R_7$ and $R_7$ are either H or $CH_3$, and
n is one to ten;

provided that $R_2$ and $R_3$ are not both simultaneously $L_3$ or $L_4$.

Prototypical macrocylic trichothecenes are Roridin A and derivatives thereof such as the 2'-oxo or the 13'-oxo derivatives. Prototypical Roridin A derivative macrocyclic trichothecenes may be characterized as follows: $R_1$ and $R_2$ are both H; $R_3$ is $CH_3$; W is $L_1$, Y is NH, $R_7$ and $R_{7'}$ are both H, n' is zero; and Z is OH;

$R_1$ and $R_2$ are both H; $R_3$ is $CH_3$; W is

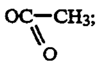

and Z is $L_1$, Y is NH, $R_7$ and $R_{7'}$ are both H, N' is zero; and $R_1$ and $R_2$ are both H; $R_3$ is $CH_3$; W is $L_3$, $R_7$ and $R_{7'}$ are both H, n is one; and Z is OH.

Acid labile linker technology, e.g., hydrazone linkers, facilitate release of therapeutic agent in target cell endosomes and lysosomes (pH 3.5–5.5) where the released agent can exert its therapeutic effect (e.g., inhibition of protein synthesis). Disulfide linkages also promote release of therapeutic agent in endosomes and lysosomes of the target cells.

Conjugates containing derivatized trichothecene molecules of the present invention may be tested as set forth below.

Immunoreactivity of the conjugates can be determined by performing a radio-labeled cell binding assay. To perform this assay, cells are incubated with a labeled antibody-derivatized trichothecene conjugate; the fraction of the bound radio-label is then determined with a gamma counter. The assay can be performed as follows:

1. Wash target cells and dilute target cells to 25–50 million cells per ml.
2. Load duplicate assay tubes (0.5 ml Eppendorf tubes) with 55 μL assay buffer (1% BSA in PBS) and 110 μL cells; load duplicate non-specific binding assay tubes with 55 μL unlabeled antibody (0.2 mg/ml) and 110 μL cells. Vortex lightly.
3. Place tubes on rotator in refrigerator and allow to mix for at least 1 hour.
4. Dilute labeled antibody conjugate to 0.160 μg/ml or 0.320 ug/ml if the specific activity is ≦0.1 mCi/mg.
5. Load 55 μL labeled conjugate into each of the 4 tubes. Vortex lightly.
6. Place tubes on rotator in refrigerator and allow to mix for a least 2 hours.
7. Prepare bullet tubes containing 150 μL of a 1:1 mixture of dibutyl phthalate and dinonyl phthalate oils. Place on ice.
8. Vortex assay tubes lightly and overlay onto oil 200 μL cell/conjugate mixture.
9. Centrifuge bullet tubes to pellet cells.
10. Slice bullet tubes above cell pellet in the oil layer.
11. Place each half in a separate glass test tube.
12. Count each tube on a gamma counter for 0.5 min.
13. Calculate percent binding ('immunoreactivity'):

$$\frac{CPM \text{ in cell pellet}}{\text{Total } CPM \text{ pellet} + \text{aqueous}}$$

14. Subtract average percent binding calculated of the blocked/non-specific bound tubes from the average percent binding calculated of the assay tubes. (% immunoreactivity)
15. Divide the % immunoreactivity by the purity (determined by ITLC) of the conjugate to calculate the adjusted immunoreactivity.

Conjugates containing derivatized trichothecene molecules, as well as the derivatized trichothecene molecules themselves may be tested as set forth in the two assays below.

To determine the efficacy of a particular derivatized trichothecene molecule, a protein synthesis inhibition assay can be performed. In this assay, cells are treated with the derivatized trichothecene molecules of the present invention for varying durations; no longer than 24 hours. After treatment, the cells are washed and incubated for 24 hours in RPMI-1640 medium. Tritiated leucine is then added for an overnight (12–18 hours) incubation. After the incubation, cells are counted on a β-counter to determine the efficacy of the treated cells as compared to untreated cells. An outline of an exemplary assay is as follows:

1. Harvest cells from tissue culture flasks and pellet by centrifugation at 750 rpm, aspirate medium.
2. Resuspend cells in PBS, pellet, and resuspend in complete RPMI-1640 medium [Whittaker Bioproducts, Walkersville, Md.] containing 10% Fetal Bovine Serum (FBS) [Whittaker BioProducts, Walkersville, Md.], 5% Serum Plus TM medium supplement [JRH Biosciences, Lenexa, Kans.], 1% Sodium pyruvate [Sigma, St. Louis, Miss.], 1% Penicillin/Streptomycin solution [Sigma, St. Louis, Miss.], and 1% L-Glutamine [Whittaker Bioproducts, Walkersville, Md.].
3. Plate 100 μl of cell suspension onto a 96 well microtiter plate.
4. Incubate cells for four hours to overnight in a humidified 37° C., 5% $CO_2$ chamber.
5. Dilute derivatized trichothecene molecules serially 10 fold from desired starting concentration in the RPMI-1640. Add medium to those wells used for the control/nontreated group.
6. Add 100 μl of compound to each well, in triplicate. Incubate in a humidified 37° C., 5% $CO_2$ chamber for a desired period of time.
7. If a suspension cell line is used, pellet cells by centrifugation at 1000 rpm and gently aspirate off the medium. If a monolayer cell line is used, aspirate off the medium.
8. Add 200 μl of PBS to each well.
9. Remove PBS as in step 7.
10. Add 100 μl of leucine-free RPMI-1640 containing 5% Serum Plus TM medium supplement, 1% Sodium pyruvate, 1% Penicillin/Streptomycin solution, 1% L-Glutamine and 1 uCi/ml of $^3$H leucine to each well. Incubate plates overnight.

12. Harvest cells onto glass fiber filters, air dry, and add to scintillation vial containing scintillation cocktail and count on a β-counter.

The efficacy of the molecule is then determined by comparing treated cells versus nontreated (control) cells.

The impact of derivatized trichothecenes of the present invention on prolonged cell death can be measured by $^3H$ leucine incorporation. Cells can be treated with the derivatized trichothecene molecules at varying concentrations. The cells are then incubated for several days in complete medium. Fresh medium is added as needed. After incubation, $^3H$ leucine in leucine-free RPMI-1640 medium is added to the cells and the cells are incubated overnight (12–18 hours). The cells are then counted on a β-counter for leucine incorporation. The procedure is an example of an assay of this type:

1. Harvest cells from tissue culture flasks and pellet by centrifugation at 750 rpm.
2. Resuspend cells in PBS, pellet, and resuspend in complete RPMI-1640 medium containing 10% FBS, 5% Serum Plus™ medium supplement, 1% Sodium pyruvate, 1% Penicillin/Streptomycin, and 1% L-Glutamine.
3. Place $1\times10^6$ cells/ml in a 5 ml snap cap tube and incubate in a humidified 37° C., 5% $CO_2$ chamber.
4. Treat cells with derivatized trichothecene molecules at log 10 dilutions starting with 1 ug/ml. Incubate for 24 hours. Dilutions should be performed in triplicate. The control tubes should be given the corresponding volume of medium.
5. Pellet cells and aspirate off the medium. Wash twice with medium.
6. Place 1 ml of complete RPMI-1640 medium in each tube and incubate for three days.
7. Pellet cells, aspirate off the medium and place another 1 ml of complete RPMI-1640 medium in each tube and incubate for two days.
8. After two days, pellet cells and wash twice with PBS.
9. Add 300 μl of leucine free RPMI-1640 medium containing 5% Serum Plus™ medium supplement, 1% Sodium pyruvate, 1% Penicillin/Streptomycin, 1% L-Glutamine and 1 uCi/ml of $^3H$ leucine and incubate overnight (12–18 hours).
10. Place cells on a 96 well microtiter plate, harvest the cells onto glass fiber filters, allow cells to dry onto the filters and add the filters to scintillation vials containing scintillation cocktail. Count on the β-counter for leucine incorporation.

Exemplary protocols for simple and macrocyclic trichothecene-linker preparation are discussed in Example VII. Exemplary protocols for trichothecene-antibody conjugation are set forth in Example VIII (A and B). The following examples are offered by way of illustration and not by way of limitation.

Example I

Verrucarol

Verrucarol is a simple, poorly cytotoxic trichothecene. It is conjugated to anti-melanoma monoclonal antibody 9.2.27 using a carbodiimide. More specifically, antibody (10 mg) in 2 ml of 0.1M NaCl was mixed with 5 mg of trichothecene (in 0.1 ml of DMSO and 1 ml of 0.1M sodium phosphate buffer, pH 6.0) and 30 mg of 1-ethyl-3,3-dimethylamino-propylcarbodiimide. The mixture was stirred at room temperature for 24 hours. After reaction, the solution was dialyzed against 0.1M sodium phosphate, pH 7.0.

Primary or secondary hydroxyl groups of the trichothecene molecule react with the carbodiimide to form derivatized trichothecene. This derivatized trichothecene molecule then reacts with lysine on the antibody to form the conjugate. Titration of the conjugate against antigen-positive and antigen-negative melanoma cells indicated an inhibitory dose ($ID_{50}$) of $10^{-8}$M. In comparison, the drug verrucarol alone has an $ID_{50}$ of $10^{-5}$M or greater when tested in the same assay.

Example II

Verrucarin A

Verrucarin A or its hemisuccinate is conjugated to monoclonal antibody 9.2.27 by the same method as stated as follows: A solution of 0.375 mM trichothecene in dry $CHCl_3$ (1 ml) was mixed with 0.45 mM succinic anhydride (1.2 eqnts.) and a catalytic amount of dimethyl amino pyridine. The mixture was held at reflux overnight, diluted to 30 ml with $CH_2Cl_2$, and washed with 10 ml 5% av. HCl. The organic layer was dried with $Na_2SO_4$, concentrated, and the resulting gum subjected to preparative TLC (silica gel, 2 mm; ethyl acetate:hexane—1:1). The trichothecene hemisuccinate was recovered in 80% yield after recrystallization from $CH_2Cl_2$/hexane/ether. Increasing titers of the conjugate are incubated with the antigen-positive and antigen-negative melanoma cells and then tested for potency and selectivity as described herein. The $ID_{50}$ against the antigen-positive cells was $10^{-7}$M or better, while there was no toxicity against the antigen-negative cells. Verrucarin A itself yielded an $ID_{50}$ of $2.5\times10-11$M.

Example III

Conjugation via cis-Aconityl Linkages

Verrucarol is covalently linked to cis-aconitic anhydride using standard procedures, such as that described above for the preparation of hemisuccinate. Alternatively, the N-hydroxysuccinimidate ester of verrucarol may be reacted with a diamine. Verrucarin A (VA) N-hydroxysuccinimidate dissolved in 2 ml of tetrahydrofuran is added to 0.36 mM each of N-hydroxysuccinimide and dicyclohexyl carbodiimide. The mixture is allowed to stand at room temperature for 6 hours, filtered to remove N-N-dicyclohexyl urea and concentrated. The N-hydroxysuccinimidate was isolated by preparative layer chromoatography using an EtAc/-hexane solvent system on a silica gel plate (2 mm). Final purification was achieved by recrystallization from diethyl ether to give about 70% yield. The derivatized trichothecene ester may then be covalently linked to cis-aconitic anhydride through the free amino group. The cis-aconityl moieties of either derivatized trichothecene may then be covalently linked to antibody using a carbodiimide linking molecule, as described in Example I.

Example IV

Glycosylation of Anguidine

Anguidine, a simple trichothecene, is poorly soluble, but glycosylation of anguidine improves solubility. Anguidine is glycosylated according to the method of W. R. Roush et al., *J. Am. Chem. Soc.* 107:3354-3355, 1985.

Briefly, anguidine (12 μM) is incubated with uridine 5'-diphosphoglucuronic acid (12 mM), B-naphthoflavone-induced hepatic microsomes from male rates (0.6 mg of protein/ml), $MgCl_2$ (2.5 mM), and $K_2HPO_4$ (10 mM, pH 7.7) at 37° C. for 3.5 hours. Using the procedure, anguidine glucuronide can be formed in approximately 60% yield. Glycosylated anguidine may then be conjugated to antibody hemisuccinate derivatives of anguidine, according to Example II.

Example V

Reduction of Intoxification

Verrucarin A-antibody conjugates are administered intravenously to a warm-blooded animal, in order to inhibit antigen-positive cells. Metabolic processes of the recipient animal may cause the premature release of the trichothecene portion of the conjugate, resulting in toxicity to cells that are not antigen-positive.

The intoxification that may result from the release of unconjugated trichothecene may be reduced by administration of anti-trichothecene antibody. Briefly, either at a predetermined time after injection of a verrucarin A-antibody conjugate, or upon detection of toxicity symptoms in a recipient, antibody capable of binding to and blocking the toxicity of verrucarin A is injected into the recipient.

Alternatively, either at a predetermined time after injection of conjugate or upon symptoms of toxicity, an intoxified recipient's plasma may be passed through an affinity column containing immobilized anti-verrucarin A antibody. The affinity column binds verrucarin A, thereby reducing the level of free verrucarin A in the plasma. The plasma is then infused back into the recipient.

Example VI

Reduction of Gastrointestinal Levels of Verrucarin A

Injection of verrucarin A-antibody conjugates into a recipient may result in the release of free verrucarin A into the gut of the recipient. The toxicity of the released verrucarin A may be decreased through a reduction of gastrointestinal levels of the free trichothecene (as described, for example, in Buck and Bratich, *Vet. Med.* 81:73-77, 1986). This may be accomplished by orally administering activated charcoal to an intoxified recipient. Activated charcoal binds free verrucarin A, thus preventing absorption from the gastrointestinal tract. The recipient is then given an oral cathartic, which facilitates the movement of the activated charcoal-trichothecene complexes through the gut.

Example VII

Preparation of Trichothecene-Linker Molecules

A. Preparation of 3-(2-Pyridinyldithio)propanoic acid. Five grams (52.2 mmol) of 3-mercaptopropanoic acid [Aldrich Chemical Co., Milwaukee, Wis.] in 75 ml of dry methylene chloride was added to a solution of 5.96 g (52.2 mmol) of methoxycarbonylsulfenyl chloride [Fluka Chemika, Long Island, N.Y.] in 150 ml of dry methylene chloride. The mixture was stirred at 15°-25° C. for 90 minutes and then concentrated. The residue was redissolved in 150 ml of dry methylene chloride and dropwise treated with 5.80 g (52.2 mmol) of 2-mercaptopyridine [Aldrich Chemical Co., Milwaukee, Wis.] in 75 ml of dry methylene chloride. The mixture was stirred at 15°-25° C. for 18 hours and concentrated to afford 11.2 g of the product as a pale yellow oil (99%).

B. Preparation of 3-(2-pyridinyldithio)propanoic acid hydrazide

Dry triethylamine, 3.76 g (37.2 mmol), was added to a solution of 8.00 g (37.2 mmol) of 3-(2-pyridinyldithio)-propanoic acid in 100 ml of dry tetrahydrofuran (THF). The mixture was cooled in an ice bath followed by the addition of 5.08 g (37.2 mmol) of isobutyl chloroformate. The mixture was stirred for 5-10 minutes, and 4.92 g (37.2 mmol) of tert-butyl carbazate was added. The resultant mixture was stirred at 15°-25° C. for 1 hour and then concentrated. The residue was diluted with 200 ml of methylene chloride and washed with water (2×100 ml). The organic phase was dried over magnesium sulfate, filtered and concentrated. The residue was dissolved in ice-cold trifluoroacetic acid (160 ml) and stirred for 10 minutes after dissolution was complete. The mixture was concentrated, and the residue was chromatographed on silica gel, eluting with 85:14:1 chloroform:methanol:ammonium hydroxide, to afford 4.25 g of the product as a pale yellow solid (50%): TLC-$R_f$0.55 (85:15:1 chloroform/methanol/ammonium hydroxide).

C. Preparation of Hydrazone Derivative of 3-Dehydroanguidine and 3-(2-Pyridinyldithio)propanoic Acid Hydrazide 100 microliters (0.708 mmol) of trifluoroacetic anhydride at −70° C. was added to a solution of 100 microliters of dry dimethylsulfoxide (1.41 mmol) in 3 ml of dry methylene chloride. The mixture was stirred at −70° C. for 10 minutes and then 70 mg (0.1.98 mmol) of anguidine [Sigma, St. Louis, Miss.] in 2 ml of dry methylene chloride was added over a period of 2-3 minutes. The resultant mixture was stirred at −70° C. for 15 minutes and then 20 microliters of dry triethylamine was added. The mixture was stirred at −70° C. for 15 minutes and at −70° C. to 15° C. for 60 minutes. The resultant mixture was diluted with 50 ml of methylene chloride and washed with 1N aqueous HCL (50 ml). The organic phase was dried over magnesium sulfate, filtered and concentrated to afford crude 3-dehydroanguidine. The crude material was dissolved in 3 ml of dry methanol and treated with 100 mg (0.436 mmol) of 3-(2-pyridinyldithio)propanoic acid hydrazide followed by 0.021 mmol of trifluoroacetic acid in 100 microliters of methanol. The mixture was stirred at 15°-25° C. for 5 hours and then concentrated. The residue was chromatographed on silica gel, eluting with 75% ethyl acetate/-hexane, to afford 67 mg of the product, a foamy white solid, as a mixture of syn and anti isomers (60%): TLC-$R_f$0.43 and 0.60 (75% ethyl acetate/hexane).

D. Preparation of a Hydrazone Derivative of 2'-dehydro-Roridin A.

1. Preparation of 13'-O-tert-butyldimethylsilyl-Roridin A. 100 mg (1.47 mmol) of imidazole was added to a solution of 232 mg (0.436 mmol) of Roridin A in 3 ml of dry dimethylformamide. The mixture was cooled to −5° C. and then 72 mg (0.478 mmol) of tertbutyldimethylsilyl chloride [Aldrich Chemical Co., Milwaukee, Wis.] was added. The resultant mixture was stirred at −5° C. to 5° C. for 4 hours and then concentrated. The residue was chromatographed on silica gel, eluting first with 30% ethyl acetate/hexane, next with 50% ethyl acetate/hexane and finally with 70% ethyl acetate/hexane, to afford 137 mg of the product as a foamy white solid (49%): TLC-$R_f$ 0.32 (30% ethyl acetate/hexane).

2. Preparation of 2'-dehydro-13'-O-tert-butyldimethylsilyl-Roridin A. At −70° C., 150 microliters (1.06 mmol) of trifluoroacetic anhydride was added to a solution of 100 microliters (1.41 mmol) of dry dimethylsulfoxide in 3 ml of dry methylene chloride. The mixture was stirred at −70° C. for 15 minutes and then 100 mg (0.155 mmol) of 13'-O-tert-butyldimethylsilyl-Roridin A in 2 ml of dry methylene chloride was added. The resultant mixture was stirred at −70° C. for 15 minutes and then 300 microliters (2.15 mmol) of dry triethylamine was added. This mixture was stirred at −70° C. for 30 minutes and at −70° C. to 15° C. for 30 minutes. The resultant mixture was then concentrated and the residue was chromatographed on silica gel, eluting with 30% ethyl acetate/hexane, to afford 82 mg of the product as a foamy white solid (82%): TLC-$R_f$0.51 (30% ethyl acetate/hexane).
3. Preparation of 2'-dehydro-Roridin A. 5 ml of 3:1:1 acetic acid:THF:water was added to a 10 ml round bottom flask, charged with 62 mg (0.096 mmol) of 2'-dehydro-13"-O-tert-butyldimethylsilyl-Roridin A. The mixture was stirred at 45°–50° C. for 4.5 hours, cooled and concentrated. The residue was chromatographed on silica gel, eluting with 5% methanol/methylene chloride, to afford 36 mg of the product as a foamy white solid (70%): TLC-$R_f$ 0.48 (5% methanol/methylene chloride).
4. Preparation of a hydrazone derivative of 2'-dehydro-Roridin A and 3-(2-pyridinyldithio)propanoic acid hydrazide. To a solution of 25 mg (0.471 mmol) of 2'-dehydro-Roridin A in 2 ml of dry methanol was added 30 mg (0.131 mmol) of 3-(2-pyridinyldithio) propanoic acid hydrazide followed by 0.013 mmol trifluoroacetic acid. The mixture was stirred at 15°–25° C. for 4 hours and then concentrated. The residue was chromatographed on silica gel, eluting with 75% ethyl acetate/hexane, to afford 25 mg of the product as a mixture of syn and anti isomers (71%): TLC-$R_f$0.29 and 0.53 (75% ethyl acetate/hexane).

E. Preparation of a Hydrazone Derivative of 2'-O-Acetyl-13'-Dehydro-Roridin A

1. Preparation of 2'-O-acetyl-13'-O-tert-butyl dimethylsilyl-Roridin A. To a solution of 159 mg (0.246 mmol) of 13'-O-tert-butyldimethylsilyl Roridin A in 4 ml of dry methylene chloride was added 200 microliters (1.43 mmol) of triethylamine, 2 mg (0.019 mmol) of dimethylaminopyridine and 120 microliters (1.27 mmol) acetic anhydride. The mixture was stirred at 15°–25° C. for 16 hours and then concentrated. The residue was chromatographed on silica gel, eluting first with 30% ethyl acetate/hexane and then with 50% ethyl acetate/hexane, to afford 156 mg of the product as a foamy white solid (92%): TLC-$R_f$0.50 (30% ethyl acetate/hexane).
2. Preparation of 2'-O-acetyl-Roridin A. To a solution of 156 mg (0.226 mmol) of 2'-O-acetyl-13'-tert-butyldimethylsilyl-Roridin A in 3 ml of dry THF was added 1.5 ml of 1M tetrabutyl ammonium fluoride. The mixture was stirred at 15°–25° C. for 4 hours and then concentrated. The residue was chromatographed on silica gel, eluting with 50% ethyl acetate/hexane, to afford 125 mg of the product as a foamy white solid (96%): TLC-$R_f$0.17 (50% ethyl acetate/hexane).
3. Preparation of 2'-O-acetyl-13'-dehydro-Roridin A. To a solution of 62 microliters (0.87 mmol) of dry dimethylsulfoxide in 2 ml of dry methylene chloride at −70° C. was added 62 microliters (0.439 mmol) trifluoroacetic anhydride. The mixture was stirred at −70° C. for 10 minutes followed by the addition of 25 mg (0.044 mmol) of 2'-O-acetyl-Roridin A in 1.5 ml of dry methylene chloride over a 2–3 minute period. This mixture was stirred at −70° C. for 20 minutes and then 180 microliters (1.29 mmol) of dry triethylamine was added. The resultant mixture was stirred at −70° C. for 15 minutes and at −70° C. to 15° C. for 20 minutes and then concentrated. The residue was chromatographed on silica gel, eluting with 5% methanol/methylene chloride, to afford 21 mg of the product as a foamy white solid.
4. Preparation of a hydrazone derivative of 2'-O-acetyl-13'-dehydro-Roridin A and 3-(2-pyridinyldithio) propanoic acid hydrazide. To a solution of 21 mg (0.037 mmol) of 2'-O-acetyl-13'-dehydro-Roridin A in 3 ml of dry methanol was added 25 mg (0.11 mmol) of 3-(2-pyridinyldithio)propanoic acid hydrazide followed by 0,011 mmol of trifluoroacetic acid in 100 microliters of dry methanol. The mixture was stirred at 15°–25° C. for 3 hours and then concentrated. The residue was chromatographed on silica gel, eluting first with 75% ethyl acetate/hexane and then with ethyl acetate, to afford 18 mg of the product as a colorless oil (62%): TLC-$R_f$0.30 (75% ethyl acetate/hexane).

F. Preparation of 2'-Desoxy-2'-alpha-(N-hydroxysuccinimidyl-3-dithio-propanoic acid)-Roridin A.

1. Preparation of 2'-desoxy-2'-beta-iodo-13'-O-tert-butyldimethylsilyl-Roridin A. To a solution of 99 mg (0.153 mmol) of 13'-O-tert-butyldimethylsilyl-Roridin A in 5 ml of dry methylene chloride at 0° C. was added 80 microliters (0,459 mmol) of dry diisopropylethylamine followed by 51 microliters (0.303 mmol) of trifluoromethanesulfonic anhydride. The mixture was stirred at 0° C. for 30 minutes and then diluted with 30 ml of methylene chloride and washed with 20 ml of 1N aqueous HCl. The organic phase was dried over magnesium sulfate, filtered and concentrated. The residue was diluted with 5 ml of acetone and then 235 mg (1.72 mmol) of sodium iodide. The mixture was stirred at reflux for 20 minutes and then diluted with 50 ml of methylene chloride and washed with 25 ml of water. The organic phase was dried over magnesium sulfate, filtered and concentrated. The residue was chromatographed on silica gel, eluting with 30% ethyl acetate/hexane to afford 95 mg of the product as a foamy white solid (87%): TLC-$R_f$0.55 (35% ethyl acetate/hexane).
2. Preparation of 2'-desoxy-2'-beta-iodo-Roridin A. To 95 mg (0,126 mmol) of 2'-desoxy-2'-beta-iodo-13'-O-tert-butyldimethylsilyl-Roridin A was added 5 ml of 3:1:1 acetic acid:THF:water. The mixture was stirred at 60°–65° C. for 4 hours and then concentrated. The residue was chromatographed on silica gel, eluting with 60% ethyl acetate/hexane, to afford 67 mg of the product as a foamy white solid (83%).
3. Preparation of 2'-desoxy-2'-alpha-thioacetyl-Roridin A. To a solution of 67 mg (0.104 mmol) of 2'-desoxy-2'-beta-iodo-Roridin A in 5 ml of absolute ethanol was added 240 mg (2.10 mmol) of potassium thioacetate. The mixture was stirred at 65°–70° C. for 5 hours, cooled, diluted with 50 ml of methylene chloride and washed with 50 ml of water. The organic phase was dried over magnesium sulfate, filtered and concentrated. The residue was chromatographed on silica gel, eluting with 60% ethyl acetate/hexane, to afford 58 mg of the product as a foamy white solid (94%): TLC-$R_f$ 0.53 (60%ethyl acetate/hexane).

4. Preparation of 2'-desoxy-2'-alpha-mercaptyl-Roridin A. To a solution of 57 mg (0.097 mmol) of 2'-desoxy-2'-alpha-thioacetyl-Roridin A in 4 ml of ethanol was added 2 ml of 28% aqueous ammonium hydroxide. The mixture was stirred at 65°–70° C. for 6 hours. The mixture was concentrated and the residue was chromatographed on silica gel, eluting with 10% ethyl acetate/hexane, to afford 25 mg of an intermediate disulfide. The disulfide was diluted into 3 ml of methylene chloride and 0.5 ml of methanol and 25 microliters (0.10 mmol) of tributylphosphine was added. The mixture was stirred at 15°–25° C. for 15 minutes and then concentrated. The residue was chromatographed on silica gel, eluting with 60% ethyl acetate/hexane, to afford 23 mg of the product as a colorless oil (43%): TLC-$R_f$ 0.39 (60% ethyl acetate/hexane).
5. Preparation of 2'-desoxy-2'-alpha-(3-dithiopropanoic acid)-Roridin A. To a solution of 21 mg (0.038 mmol) of 2'-desoxy-2'-alpha-mercaptyl-Roridin A in 3 ml of ethanol was added 20 mg (0.093 mmol) of 3-(2-pyridinyldithio)propanoic acid followed by 25 microliters (0.179 mmol) of triethylamine. The mixture was stirred at 15°–25° C. for 30 minutes and then diluted with 50 ml of ethyl acetate and washed with 10 ml of 1N aqueous HCl. The organic phase was dried over magnesium sulfate, filtered and concentrated. The residue was chromatographed on silica gel, eluting first with 0.1% acetic acid/ethyl acetate and then with 0.1:5::95 acetic acid:methanol:ethyl acetate, to afford 22 mg of the product as a near colorless oil (88%): TLC-$R_f$ 0.37 (0.1:5:95 acetic acid:methanol:ethyl acetate).
6. Preparation of 2'-desoxy-2'-alpha-(N-hydroxy succinimidyl-3-dithiopropanoic acid)-Roridin A. To a solution of 22 mg (0.0337 mmol) of 2'-desoxy-2'-alpha-(3-dithiopropanoic acid)-Roridin A in 2 ml of dry THF was added 12 mg (0.104 mmol) of N-hydroxysuccinimide followed by 18 mg (0.087 mmol) of dicyclohexyl carbodiimide. The mixture was stirred at 15°–25° C. for 4 hours and then 20 microliters of acetic acid was added. The mixture was stirred an additional 30 minutes and then filtered through a plug of glass wool. The solids were washed with 3 ml of THF. The filtrates were combined and concentrated. The residue was chromatographed on silica gel, eluting first with 0.1:50:50 acetic acid:ethyl acetate:hexane and then with 0.1% acetic acid/ethyl acetate, to afford 18 mg of the product as a white solid (71%): TLC-$R_f$ 0.69 (ethyl acetate).

EXAMPLE VIII

Preparation of Trichothecene-Containing Conjugates

Conjugation of trichothecenes as described in the specification may be conducted through either of two exemplary synthesis schemes: (1) reaction of the amino groups of a targeting moiety with N-hydroxy succinimidate (NHS)-derivatized trichothecenes or (2) the reaction of reduced disulfides or free sulfhydryls of a targeting moiety with 2-pyridinyl dithio-derivatized trichothecenes.

A. Antibody Conjugation of NHS-Derivatized Trichothecenes

This conjugation was generally performed in 6.2 mM sodium borate buffer (0.5M, pH 8) containing the antibody stabilizer molecusol at 1% wt/vol. The NHS-derivatized trichothecene dissolved in 100% DMSO was added dropwise to a stirred solution of antibody at a final antibody concentration of 1.0 mg/ml reaction solution. To achieve a trichothecene loading of 6–9/antibody, NHS-derivatized trichothecene was offered at a 30:1 trichothecene:antibody molar ratio at a final concentration of 25% DMSO (v/vol.). The reaction mixture was incubated with continuous stirring at room temperature for 1 hour prior to purification by size exclusion chromatography, extensive dialysis, concentration via membrane centrifugation and sterile filtration. Conjugates thus prepared were stored refrigerated (e.g., at 5°–10° C.) or quick frozen in liquid nitrogen and then stored at −70° C. until use.

Specifically for succinimidyl-2'-Roridin A-3-dithiopropionate conjugation to antibody, 0.40 ml of 6.2 mM sodium borate buffer (0.5M, pH 8.0) and 0.20 ml of 100 mg molecusol/ml $H_2O$ were added to 1.0 ml of 2.0 mg NR-LU-10/ml in PBS (i.e., 6.2 mM sodium phosphate, 150 mM NaCl, pH 7.2). 0.50 ml of DMSO having 290 micrograms of succinimidyl-2'-Roridin A-3-dithiopropionate dissolved therein (for a 30:1 trichothecene:antibody molar offering ratio) was added dropwise and with stirring over a 10 second time period. To purify the resultant product, 1 ml aliquots of reaction solution were applied to PD-10 Sephadex® columns [Pharmacia, Uppsala, Sweden] equilibrated in PBS containing 1% molecusol (wt/vol). The eluted conjugate was collected in the 2.4–4.8 ml fraction. The PD-10 purified aliquots were then pooled, exhaustively dialyzed against PBS containing 1% molecusol (wt/vol) using Spectra/POR molecular porous membrane tubing (Spectrum Medical Industries, Inc., Los Angeles, Calif.), concentrated on a Centricon™ PM-30 microconcentrator [Amicon Div., W. R. Grace & Co., Beverly, Mass.], and sterile filtered using a 2.2 micron Acrodisc [Gelman Sciences, Ann Arbor, Mich.]. Conjugates thus prepared were stored refrigerated (e.g., at 5°–10° C.) or quick frozen in liquid nitrogen and then stored at −70° C. until use.

B. Antibody Conjugation of 2-Pyridinyl-Dithio-Derivatized Trichothecenes

In conjugation of 2-pyridinyl-dithio-derivatized trichothecenes, NR-LU-10 disulfides were first reduced by incubating NR-LU-10 at 5–10 mg in 1 ml of PBS containing 10–15 mM dithiothreitol for 15 minutes at room temperature. The reduced product was purified over a PD-10 column that had been equilibrated in degassed 0.1M sodium phosphate, pH 7.5, containing 0.1M NaCl, 1% molecusol and 0.2 mM EDTA (Na salt). Immediately after reduced-disulfide NR-LU-10 purification, dropwise addition of 2-pyridinyl-dithio-derivatized trichothecene dissolved in DMSO (0.40 ml of DMSO, containing 432 micrograms of 3-(2-pyridinyldithio) propionate hydrazide-2'-Roridin A hydrazone or containing 337 micrograms of 3-(2-pyridinyldithio) propionate hydrazide-3-anguidine hydrazone or containing 459 micrograms of 3-(2- pyridinyldithio) propionate hydrazide-2'-acetyl-13'-Roridin A hydrazone) to 2 mg of the reduced disulfide NR-LU-10 solution (a 44:1 trichothecene:antibody molar offering ratio) was conducted with stirring. Generally in conducting the conjugation, the reaction concentration of antibody was 0.8–1.2 mg/ml, DMSO was 16–25% (vol/vol), and trichothecene to antibody molar offering ranged from 40:1 to 50:1 (in order to achieve a loading of approximately 6 trichothecenes per antibody). After 1 hour of incubation at room temperature, purification proceeded analogously to the purification scheme described in Example VII(A) above. Conjugates thus prepared were stored refrigerated (e.g., at 5°–10° C.) or quick frozen in liquid nitrogen and then stored at −70° C. until use.

From the foregoing it will be appreciated that, although specific embodiments of the invention have been described herein for purposes of illustration, various modifications may be made without deviating from the spirit and scope of the invention.

What is claimed is:

1. A trichothecene compound of the following formula:

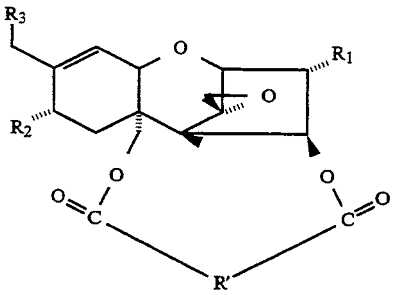

wherein R' is selected from the group consisting of

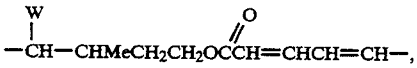,

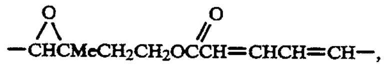,

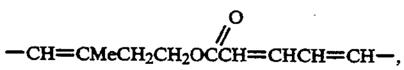,

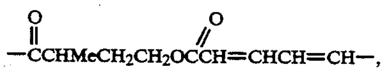, or

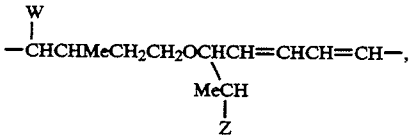, provided at least one of $R_1$, W and Z is $L_2$, $L_3$, or $L_4$, and further provided W and Z are not both $L_2$, $L_3$, or $L_4$ wherein $L_2$ is

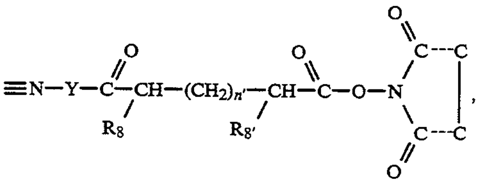, $L_3$ is

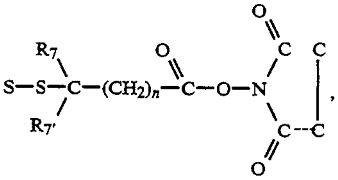, or $L_4$ is

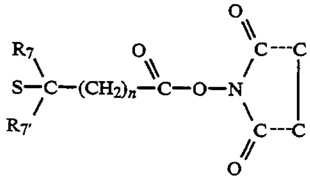, and wherein

Y is O or NH, $R_7$ or $R_{7'}$ is H or $CH_3$, $R_8$ or $R_{8'}$ is H or OH, n is one to ten; and n' is zero to ten;

and further provided that W and Z can be independently either H, OH, or SH when W and Z are not $L_2$, $L_3$, or $L_4$; $R_1$ is H, OH, or SH when R1 is not $L_2$, $L_3$, or $L_4$; and $R_2$ and $R_3$ are selected from the group consisting of H, OH, SH, $OCH_3$, $SCH_3$, $NH_2$, $NHCH_3$, $N(CH_3)_2$, $L_3$ and $L_4$.

2. A trichothecene compound of claim 1 wherein R' is

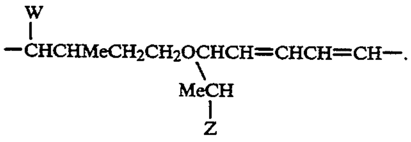.

3. A trichothecene compound of claim 2, wherein $R_1$ is $L_2$, $R_3$, or $L_4$ wherein Y is O or NH, $R_7$ and $R_{7'}$ are independently either H or $CH_3$, $R_8$ and $R_{8'}$ are independently either H or OH, n is one to ten, n' is zero to ten;

when $R_2$ and $R_3$ are selected from the group consisting of, H, OH, SH, $OCH_3$, $SCH_3$, NH, $NHCH_3$, $N(CH_3)_2$; and W and Z are independently either H, OH, or SH.

4. A trichothecene compound of claim 2 wherein $R_1$ and W are independently either H, OH, or SH; $R_2$ and $R_3$ are selected from the group consisting of, H, OH, SH, $OCH_3$, $SCH_3$, $NH_2$, $NHCH_3$, $N(CH_3)_2$; and Z is $L_2$, $L_3$, or $L_4$ and wherein Y is O or NH, $R_7$ or $R_7$, is H or $CH_3$, $R_8$ or $R_8$, is H or OH, n is one to ten; and n' is zero to ten.

5. A trichothecene compound of claim 2 wherein $R_1$ and Z are H, SH, or OH; $R_2$ and $R_3$ are selected from the group consisting of H, H, SH, $OCH_3$, $SCH_3$, $NH_2$, $NHCH_3$, $N(CH_3)_2$; and W is either $L_2$, $L_3$, or $L_4$ and wherein Y is O or NH, $R_7$ or $R_7$, is H or $CH_3$, $R_8$ or $R_8$, is H or OH, n is one to ten, and n' is zero to ten.

6. A trichothecene compound of claim 2 wherein $R_1$, W and Z are independently either SH or OH; $R_2$ and $R_3$ are selected from the group consisting of H, OH, SH, $OCH_3$, $SCH_3$, $NH_2$, $NHCH_3$, $N(CH_3)_2$, $L_3$, and $L_4$ wherein $R_7$ and $R_7$, are either H or $CH_3$, and n is one to ten;

provided that $R_2$ and $R_3$ are not both simultaneously $L_3$ or $L_4$.

7. A trichothecene compound of claim 5 wherein $R_1$ and $R_2$ are both H; $R_3$ is $OCH_3$; W is $L_3$, $R_7$ and $R_7$, are both H, n is one; and Z is OH.

* * * * *

UNITED STATES PATENT AND TRADEMARK OFFICE

CERTIFICATE OF CORRECTION

PATENT NO. : 5,405,966

DATED : Apr. 11, 1995

INVENTOR(S) : THEODORE ET AL.

It is certified that error appears in the above-indentified patent and that said Letters Patent is hereby corrected as shown below:

Column 2, lines 37-41, please underline "N" and "M".

Column 2, line 41, please delete "M" and insert --N--therefor.

Column 2, line 46, please underline "L".

Column 8, line 65, please delete the extra period between "," and "central".

Column 11, line 34, please insert a space between "$R_2$" and "is".

Column 12, line 40, please delete extra "t" in "trichotthecenes".

Column 12, line 42, please delete the "," after $R_7$ and insert --'-- in subscript therefor.

Column 12, line 56, please delete the "," after $R_7$ and insert --'-- in subscript therefor.

Column 12, line 61, please delete the "," after $R_7$ and insert --'-- in subscript therefor.

Column 12, line 62, please delete the "," after $R_7$ and insert --'-- in subscript therefor.

Column 13, line 2, please delete "T" after, R and insert --$_{7}$'-- therefor.

Column 14, line 26, please delete the "," after $R_7$ and insert --'-- in subscript therefor.

Column 14, line 29, please delete "N" and insert --n-- therefor.

UNITED STATES PATENT AND TRADEMARK OFFICE
CERTIFICATE OF CORRECTION

PATENT NO. : 5,405,966

DATED : Apr. 11, 1995

INVENTOR(S) : THEODORE ET AL.

It is certified that error appears in the above-indentified patent and that said Letters Patent is hereby corrected as shown below:

Column 14, line 53, please delete the "," after $R_7$ and insert -- ′-- in subscript therefor.

Column 14, line 54, please delete the "," after $R_8$ and insert -- ′-- in subscript therefor.

Column 14, line 65, please delete the "," after $R_7$ and insert -- ′-- in subscript therefor.

Column 14, line 66, please delete the "," after $R_8$ and insert -- ′-- in subscript therefor.

Column 15, line 7, please delete the "," after $R_7$ and insert -- ′-- in subscript therefor.

Column 15, line 8, please delete the "," after $R_8$ and insert -- ′-- in subscript therefor.

Column 15, line 15, please insert -- ′-- after $R_7$ (second occurrence)--.

Column 15, line 24, please delete the "," after $R_7$ and insert -- ′-- in subscript therefor.

Column 15, line 31, please delete the "," after $R_7$ and insert -- ′-- in subscript therefor.

Column 15, line 33, please delete the "," after $R_7$ and insert -- ′-- in subscript therefor.

Column 18, line 36, please delete "-11" and insert --$^{-}$11-- therefor.

Column 20, line 34, please delete "." between "0" and "."

Column 22, line 25, please delete "," and insert "1" and "9"--.

Column 22, line 41, please delete "," and insert "." therefor.

UNITED STATES PATENT AND TRADEMARK OFFICE

CERTIFICATE OF CORRECTION

PATENT NO. : 5,405,966

DATED : Apr. 11, 1995

INVENTOR(S) : THEODORE ET AL.

It is certified that error appears in the above-indentified patent and that said Letters Patent is hereby corrected as shown below:

Column 22, line 59, please delete "," and insert "." therefor.

Column 23, line 38, please delete ":" between ":" and "95"

Column 26, line 5, please delete "=" and insert "=" therefor.

Column 26, line 15, please insert "---" in equation between "C" and "C".

Column 26, line 36, please delete the "," after $R_7$ and insert --′-- in subscript therefor.

Column 26, line 37, please delete the "," after $R_8$ and insert --′-- in subscript therefor.

Column 26, line 57, please delete "R" after "$L_2$," and insert --L-- therefor.

Column 26, line 59, please delete the "," after $R_7$ and insert --′-- in subscript therefor.

Column 26, line 60, please delete the "," after $R_8$ and insert --′-- in subscript therefor.

Column 27, line 4, please delete the "," after $R_7$ and insert --′-- in subscript therefor.

Column 27, line 5, please delete the "," after $R_8$ and insert --′-- in subscript therefor.

Column 27, line 10, please insert --O-- after "H," and before "H, SH, $OCH_3$".

Column 27, line 14, please delete the "," after $R_7$ and insert --′-- in subscript therefor.

UNITED STATES PATENT AND TRADEMARK OFFICE

CERTIFICATE OF CORRECTION

PATENT NO. : 5,405,966

DATED : Apr. 11, 1995

INVENTOR(S) : THEODORE ET AL.

It is certified that error appears in the above-indentified patent and that said Letters Patent is hereby corrected as shown below:

Column 27, line 15, please delete the "," after $R_8$ and insert -- ' -- in subscript therefor.

Column 28, line 8, please delete the "," after $R_7$ and insert -- ' -- in subscript therefor.

Column 28, line 13, please delete "O" after "is" and before "$CH_3$".

Column 28, line 13, please delete the "," after $R_7$ and insert -- ' -- in subscript therefor.

Signed and Sealed this

Twenty-seventh Day of August, 1996

Attest:

BRUCE LEHMAN

*Attesting Officer* *Commissioner of Patents and Trademarks*